United States Patent [19]

Hahn

[11] Patent Number: 4,692,511

[45] Date of Patent: Sep. 8, 1987

[54] PEPTIDE ANTAGONISTS FOR THE C5A ANAPHYLATOXIN

[75] Inventor: Gary S. Hahn, San Diego, Calif.

[73] Assignee: Immunetech Pharmaceuticals, San Diego, Calif.

[21] Appl. No.: 627,702

[22] Filed: Jul. 3, 1984

[51] Int. Cl.[4] .......................... C07K 5/08; C07K 5/10; C07K 7/06; C07K 7/08; C07K 7/10

[52] U.S. Cl. .................................... 530/325; 530/326; 530/327; 530/328; 530/329; 530/330; 530/331

[58] Field of Search ................. 260/112.5 R; 530/325, 530/326, 327, 328, 329, 330, 331

[56] References Cited

PUBLICATIONS

Chem. Abstr. vol. 101, (1984) 168770d.
Chem. Abstr. vol. 93, (1980) 5893y.
Chem. Abstr. vol. 103 (1985) 86252p.
Biochem. and Biophys. Res. Commun. vol. 86, (1979) 227-234.
The Journal of Biol. Chem. vol. 253, No. 19 (1978) 6955-6964.
Chem. Abstr. vol. 88, (1978) 119258.
Biochemistry, vol. 18, No. 8, (1979) 1490-1497.
Chem. Abstr. vol. 88, (1978) 119257w; 119258x.

*Primary Examiner*—Delbert R. Phillips
*Attorney, Agent, or Firm*—Lyon & Lyon

[57] ABSTRACT

Peptides and peptide compositions are disclosed which act as competitive antagonists for the C5a receptor and thus block inflammatory and immunomodulatory activity mediated by endogenous C5a.

16 Claims, 1 Drawing Figure

```
              1                    5                                  10
NH₂ - Thr - Leu - Gln - Lys - Lys - Ile - Glu - Glu - Ile - Ala -

15                           20
      Ala - Lys - Tyr - Lys - His - Ser - Val - Val - Lys - Lys - Cys -

25                           30
      Cys - Tyr - Asp - Gly - Ala - Cys - Val - Asn - Asn - Asp - Glu -

35                           40
      Thr - Cys - Glu - Gln - Arg - Ala - Ala - Arg - Ile - Ser - Leu -

45                           50
      Gly - Pro - Arg - Cys - Ile - Lys - Ala - Phe - Thr - Glu - Cys -

55                           60                (CHO)    65
      Cys - Val - Val - Ala - Ser - Gln - Leu - Arg - Ala - Asn - Ile -

70
      Ser - His - Lys - Asp - Met - Gln - Leu - Gly - Arg - OH
```

PEPTIDE ANTAGONISTS FOR THE C5A ANAPHYLATOXIN

FIELD OF THE INVENTION

The invention relates to peptides which bind to and block the C5a activity.

BACKGROUND OF THE INVENTION

The general inflammatory response of humans occurs whenever tissue is injured. The injury may be due to a wide variety of conditions including infection by bacteria, viruses or fungi, invasion by cancer cells, allergic or autoimmune diseases and physically- or chemically-induced trauma. In all of these diseases and conditions the complement system is activated resulting in production of C5a which serves to amplify and exacerbate the resulting inflammation. By binding to and blocking the C5a receptor, the peptides of the present invention can reduce or prevent C5a-mediated inflammation. In addition, these peptides may inhibit the immunoregulatory effects of C5a and thus indirectly cause immunoregulation.

The anaphylatoxin C5a is one of the more potent biologic factors known to man. This factor is generated when C5 is cleaved at a specific site by convertases (proteolytic enzymes) of the blood complement system, as well as by enzymes of the coagulation system. C5a is the last in a series of three anaphylatoxins that are released during activation of the complement cascade. Anaphylatoxins C3a and C4a, factors released prior to C5a in the activation sequence, are considerably less potent than C5a for inducing cellular histamine release and tissue spasmogenic responses, and for enhancing vascular permeability. Furthermore, C5a is the most active leukotactic factor known to originate from any blood component.

Upon release, C5a binds to its specific cellular receptors present on blood leukocytes including polymorphonuclear neutrophils, monocytes, basophils, and eosinophils, and to tissue-resident cells such as macrophages and mast cells. Such binding of C5a to its receptor triggers cells to release vasoactive and inflammatory substances including histamine, leukotrienes, prostaglandins, and proteolytic enzymes. These and other substances produce contraction of smooth muscle, platelet aggregation, vasodialation, and increased vascular permeability which results in the pain and swelling which is characteristic of inflammation. In addition, C5a is a powerful attractant of leukocytes to sites of inflammation by the process of chemotaxis which leads to an increased cellular inflammatory response. C5a also exerts immunomodulatory effects on immune responsiveness as evidenced by its ability to potentiate the primary antibody response to antigens in vitro.

SUMMARY OF THE INVENTION

The present invention provides peptides and peptide compositions which act as competitive antagonists for the C5a receptor and thus block inflammatory and immunomodulatory activity mediated by endogenous C5a.

Although the peptides of the present invention can act as inhibitors of inflammation due to many causes, these peptides are particularly useful in the treatment of diseases or conditions in which acute or chronic inflammation significantly contributes to disease symptoms and disease pathogenesis. Such diseases or conditions include, but are not limited to, autoimmune diseases including rheumatoid athritis and systemic lupus erthematosus, vasculitis, serum sickness, angiodema, bullous skin diseases, hypersensitivity pneumonitis, adult respiratory distress syndrome, idiopathic pulmonary fibrosis and immune complex-mediated glomerulonephritis.

BRIEF DESCRIPTION OF THE DRAWING

The FIGURE illustrates the amino acid sequence of native human C5a.

DETAILED DESCRIPTION OF THE INVENTION

Attempts to identify the submolecular site(s) in C5a which directly bind to the C5a receptor have produced only incomplete results. The complex oligosaccharide moiety which is linked to asparagine 64 of native C5a does not appear to form part of the C5a receptor binding site. Removal of the oligosaccharide moiety from native C5a does not change its biological activity. Surprisingly, deglycosylated C5a des Arg-74 is approximately tenfold more active than native C5a des Arg-74, indicating that the oligosaccharide may partially block or otherwise negatively modulate the bioactivity of C5a des Arg. Enzymatic removal by carboxypeptides B of the C-terminal arginine residue from the 74 residue C5a chain (FIG. 1) to produce C5a des Arg-74 resulted in reduction but not abolition of C5a's bioactivity indicating that the molecule's C-terminus was important but not required for activity. This finding is in contrast to the bioactivity of the C3a and C4a anaphylatoxins which are inactivated after removal of their C-terminal arginine. The bioactivity of C5a des Arg-74 is further reflected by its ability to bind to the neutrophil C5a receptor and to effectively compete with native C5 for its receptor. Enzymatic removal of the five C-terminal residues from human C5a produces a biofunctionally inactive derivative C5a 1-69 which continues to exhibit substantial C5a receptor binding activity. The ability of C5a 1-69 to act as a competitive antagonist with C5a for its receptor indicates that a second receptor binding site of C5a distinct from the carboxyterminus exists.

Synthetic peptides with sequences identical to portions of the C5a C-terminus exhibits no biactivity when compared to intact C5a and cannot effectively act as competitive antagonists for the C5a receptor when mixed with C5a in receptor binding or anaphylatoxin bioassays.

These results suggest that the carboxyterminal region of C5a contains residues primarily responsible for activating or triggering the C5a receptor while a separate, distinct receptor-binding site having minimal receptor activating capacity exists in more amino-terminal portions of the molecule.

Studies of cyanogen bromide cleaved porcine C5a indicate that a peptide identical to C5a amino acid sequences (aa) 2-17 has negligible C5a biological activity while a fragment representing aa 18-73 had <1% of the activity of intact C5a, indicating that the first 17 residues are not critical for C5a function.

Nitration of Tyrosine 23 of C5a des Arg-74 substantially reduced the peptide's neutrophil binding activity, providing further evidence for the importance of amino-terminal residues for receptor binding. From this data alone, however, it is unclear whether the Tyrosine in question directly binds to receptor structures or whether the chemical modification results in distortion of the C5a three-dimensional structure or perturbation of other critical residues spatially related to the Tyrosine.

In the following description, the amino acid components of the peptides are identified as abbreviations for convenience. These abbreviations are intended to include both the D- and L-forms although the L-form is preferred:

| Amino Acid | Abbreviation |
|---|---|
| L-glycine | Gly |
| L-alanine | Ala |
| L-valine | Val |
| L-leucine | Leu |
| L-isoleucine | Ile |
| L-proline | Pro |
| L-methionine | Met |
| L-cysteine | Cys |
| L-phenylalanine | Phe |
| L-tyrosine | Tyr |
| L-tryptophan | Trp |
| L-histidine | His |
| L-lysine | Lys |
| L-arginine | Arg |
| L-aspartic acid | Asp |
| L-asparagine | Asn |
| L-glutamic acid | Glu |
| L-glutamine | Gln |
| L-serine | Ser |
| L-threonine | Thr |
| L-ornithine | Orn |

Surprisingly, the present invention provides peptides and peptide compositions which act as competitive antagonists for the C5a receptor and thus block inflammatory and immunomodulatory activity mediated by endogenous C5a. In its broadest scope, the present invention provides peptides having the following formula:

A-B-C-R-D-E-F where
A is H (hydrogen) or an amino acid or polypeptide selected from the following list:

Lys—His—Ser—Val—Val—Lys—Lys—
His—Ser—Val—Val—Lys—Lys—
Ser—Val—Val—Lys—Lys—
Val—Val—Lys—Lys—
Val—Lys—Lys—
Lys—Lys—
Lys—

B is H (hydrogen) or an amino acid selected from the following list:
Cys
or
Ser

B is H (hydrogen) or an amino acid selected from the following list:
Cys
or
Ser
R is a "core" tetrapeptide:
Tyr-Asp-Gly-Ala or Asp-Gly-Ala-Tyr or a "core" tripeptide:
Asp-Gly-Ala
D is H (hydroxyl) or an amino acid selected from the following list:
Cys
Ser
or
Tyr
E is H (hydroxyl) or an amino acid selected from the following list:
Val
or
Arg
and F is H (hydroxyl) or an amino acid or polypeptide selected from the following list:
Asn-Asn-Asp-Glu-Thr-Cys-Glu-Gln-Arg
Asn-Asn-Asp-Glu-Thr-Cys-Glu-Gln
Asn-Asn-Asp-Glu-Thr-Cys-Glu
Asn-Asn-Asp-Glu-Thr-Cys
Asn-Asn-Asp-Glu-Thr
Asn-Asn-Asp-Glu
Asn-Asn-Asp
Asn-Asn
Asn or peptides identical to the first four listed in which Ser is substituted for Cys.

It is evident from this description that the invention consists of an essential "core" tetrapeptide Tyr-Asp-Gly-Ala or Asp-Gly-Ala-Tyr, or a "core" tripeptide Asp-Gly-Ala, which displays C5a blocking activity. This blocking activity is maintained or increased by amino and/or carboxyterminal additions of amino acids, or polypeptide moieties which are identical to those found in the native human C5a sequence from aa 14–37.

In addition, it was discovered that certain amino acid sequence positions in the peptides of the present invention could be substituted with amino acids not found in the native human C5a molecule. For example, all Cys residues can be substituted with Ser, an amino acid which closely resembles Cys in size and side chain configuration. The Cys corresponding to Cys 27 of native human C5a can, in addition, be substituted with Tyr, a residue which occurs at the corresponding position of porcine C5a. Similarly, the Val corresponding to Val 28 of the native human C5a sequence can also be substituted with Arg, a residue which occurs at the corresponding position of porcine C5a. For example, the following peptides which display C5a receptor blocking activity illustrate peptides of the present invention.

Asp—Gly—Ala—Cys—Val—Asn—Asn—Asp—Glu
Tyr—Asp—Gly—Ala—Cys—Val—Asn—Asn—Asp—Glu
Ser—Ser—Tyr—Asp—Gly—Ala—Cys—Val—Asn—Asn—Asp—Glu
Lys—Ser—Ser—Tyr—Asp—Gly—Ala—Cys—Val—Asn—Asn—Asp—Glu
Lys—Lys—Ser—Ser—Tyr—Asp—Gly—Ala—Cys—Val—Asn—Asn—Asp—Glu
Val—Lys—Lys—Ser—Ser—Tyr—Asp—Gly—Ala—Cys—Val—Asn—Asn—Asp—Glu
Val—Val—Lys—Lys—Ser—Ser—Tyr—Asp—Gly—Ala—Cys—Val—Asn—Asn—Asp—Glu
Ser—Val—Val—Lys—Lys—Ser—Ser—Tyr—Asp—Gly—Ala—Cys—Val—Asn—Asn—Asp—Glu
His—Ser—Val—Val—Lys—Lys—Ser—Ser—Tyr—Asp—Gly—Ala—Cys—Val—Asn—Asn—Asp—Glu
Lys—His—Ser—Val—Val—Lys—Lys—Ser—Ser—Tyr—Asp—Gly—Ala—Cys—Val—Asn—Asn—Asp—Glu
Asp—Gly—Ala—Ser—Val—Asn—Asn—Asp—Glu
Tyr—Asp—Gly—Ala—Ser—Val—Asn—Asn—Asp—Glu

-continued
```
                        Lys—Lys—Ser—Ser—Tyr—Asp—Gly—Ala—Ser—Val—Asn—Asn—Asp—Glu
            Lys—His—Ser—Val—Val—Lys—Lys—Ser—Ser—Tyr—Asp—Gly—Ala—Ser—Val—Asn—Asn—Asp—Glu
                                                            Asp—Gly—Ala
                                                        Tyr—Asp—Gly—Ala
                                                    Cys—Tyr—Asp—Gly—Ala
                                                Cys—Cys—Tyr—Asp—Gly—Ala
                                            Lys—Cys—Cys—Tyr—Asp—Gly—Ala
                                                            Asp—Gly—Ala—Tyr—Arg
                                                        Tyr—Asp—Gly—Ala—Tyr—Arg
                                                    Ser—Tyr—Asp—Gly—Ala—Tyr—Arg
                                                Ser—Ser—Tyr—Asp—Gly—Ala—Tyr—Arg
                                            Lys—Ser—Ser—Tyr—Asp—Gly—Ala—Tyr—Arg
                                        Lys—Lys—Ser—Ser—Tyr—Asp—Gly—Ala—Tyr—Arg
                                                            Asp—Gly—Ala—Tyr
                                                        Tyr—Asp—Gly—Ala—Tyr
                                                    Ser—Tyr—Asp—Gly—Ala—Tyr
                                                Ser—Ser—Tyr—Asp—Gly—Ala—Tyr
                                            Lys—Ser—Ser—Tyr—Asp—Gly—Ala—Tyr
                                        Lys—Lys—Ser—Ser—Tyr—Asp—Gly—Ala—Tyr
                                                            Asp—Gly—Ala—Ser
                                                        Tyr—Asp—Gly—Ala—Ser
                                                    Ser—Tyr—Asp—Gly—Ala—Ser
                                                Ser—Ser—Tyr—Asp—Gly—Ala—Ser
                                            Lys—Ser—Ser—Tyr—Asp—Gly—Ala—Ser
                                        Lys—Lys—Ser—Ser—Tyr—Asp—Gly—Ala—Ser
            Lys—Cys—Cys—Tyr—Asp—Gly—Ala—Cys—Val—Asn—Asn—Asp—Glu—Thr—Cys—Glu—Gln—Arg
                Cys—Cys—Tyr—Asp—Gly—Ala—Cys—Val—Asn—Asn—Asp—Glu—Thr—Cys—Glu—Gln—Arg
                    Cys—Tyr—Asp—Gly—Ala—Cys—Val—Asn—Asn—Asp—Glu—Thr—Cys—Glu—Gln—Arg
                        Tyr—Asp—Gly—Ala—Cys—Val—Asn—Asn—Asp—Glu—Thr—Cys—Glu—Gln—Arg
                            Asp—Gly—Ala—Cys—Val—Asn—Asn—Asp—Glu—Thr—Cys—Glu—Gln—Arg
                                Gly—Ala—Cys—Val—Asn—Asn—Asp—Glu—Thr—Cys—Glu—Gln—Arg
                                    Ala—Cys—Val—Asn—Asn—Asp—Glu—Thr—Cys—Glu—Gln—Arg
                                        Asn—Asn—Asp—Glu—Thr—Cys—Glu—Gln—Arg
                                            Asp—Glu—Thr—Cys—Glu—Gln—Arg
                                                Thr—Cys—Glu—Gln—Arg
                                                    Cys—Glu—Gln—Arg
```

Certain other amino acids may be substituted for those listed so long as they are "functionally conserved" in the sense that they preserve or increase the C5a receptor-blocking activities which characterize the peptides of the present invention. That is, amino acids which are chemically similar by virtue of similar side chain site, charge, shape, solubility and related characteristics may be substituted for those listed while retaining the peptide's biological activity. Groups of amino acids characterized by such chemical similarity and retention of biological activity are termed "functionally conserved," as proposed by Margaret Dayhoff, et al., "A Model of Evolutionary Change in Proteins" in the *Atlas of Protein Sequence and Structure, Volume* 5 (1972), published by the National Biomedical Research Foundation, and incorporated herein by reference. Functionally conserved groups of amino acids include:

| Group | Amino Acids |
| --- | --- |
| small aliphatic | Ala, Pro, Gly |
| acid amide | Gln, Asn |
| acid | Glu, Asp |
| hydroxyl | Ser, Thr |
| sulfhydral | Cys |
| aliphatic | Val, Ile, Leu, Met |
| basic | Lys, Arg, His |
| aromatic | Phe, Tyr, Trp |

Functionally conserved groups of amino acids need not be limited to the 20 amino acids listed above. Other amino acids having chemical properties and biological effects similar to one of the eight groups listed above may also be substituted within a particular group for the listed amino acids. For example, ornithine and homoarginine have basic side chains similar to Lys, Arg, and His and may be substituted therefor while retaining the peptide's biological activity. In addition, it is within the scope of the present invention that other moieties such as fatty acids or lipophilic polypeptides or amphipathic polypeptides which increase the ability of the peptides of the present invention to non-specifically bind to lipids of cell surface membranes may be covalently added to either the amino or carboxy-terminal ends of the C5a-blocking peptides to increase their activity.

Within the general sequence
A-D-C-R-D-E-F
it is preferred that:

A is Val—Val—Lys—Lys,
    Val—Lys—Lys,
        Lys—Lys, or
           Lys
B is Ser
C is Ser
D is Ser or Tyr
E is Val, and
F is Asn—Asn, or
    Asn It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A peptide antagonist for C5a activity, said peptide having an amino acid sequence A-B-C-R-D-E-F wherein:

A is an amino-terminal hydrogen or an amino acid or polypeptide selected from the following list:

Lys—His—Ser—Val—Val—Lys—Lys—
          His—Ser—Val—Val—Lys—Lys—
               Ser—Val—Val—Lys—Lys—
                    Val—Val—Lys—Lys—
                         Val—Lys—Lys—
                             Lys—Lys—
                                 Lys—;

B is said amino-terminal hydrogen or an amino acid selected from the following list:
Cys
or
Ser;
C is said amino-terminal hydrogen or an amino acid selected from the following list:
Cys
or
Ser
R is a "core" tetrapeptide:
Tyr-Asp-Gly-Ala or Asp-Gly-Ala-Tyr
or a "core" tripeptide:
Asp-Gly-Ala;
D is a carboxy-terminal hydroxyl or an amino acid selected from the following list:
Cys
Ser
or
Tyr;
E is said carboxy-terminal hydroxyl or an amino acid selected from the following list:
Val
or
Arg;
F is said carboxy-terminal hydroxyl or an amino acid or polypeptide selected from the following list:
Asn-Asn-Asp-Glu-Thr-Cys-Glu-Gln-Arg
Asn-Asn-Asp-Glu-Thr-Cys-Glu-Gln
Asn-Asn-Asp-Glu-Thr-Cys-Glu
Asn-Asn-Asp-Glu-Thr-Cys
Asn-Asn-Asp-Glu-Thr
Asn-Asn-Asp-Glu
Asn-Asn-Asp
Asn-Asn
Asn and polypeptides identical to the first four listed in which Ser is substituted for Cys; and wherein the above amino acids and polypeptides are composed of L-enantiomeric amino acids.

2. The peptide antagonist of claim 1, wherein R is Tyr-Asp-Gly-Ala.

3. The peptide antagonist of claim 1, wherein R is Asp-Gly-Ala-Tyr.

4. The peptide antagonist of claim 1, wherein R is Asp-Gly-Ala.

5. The peptide antagonist of claim 1, 2, 3 or 4 wherein A is selected from the group consisting of Val—Val—Lys—Lys,
        Val—Lys—Lys,
            Lys—Lys, and
                Lys.

6. The peptide antagonsit of claim 2, wherein A is selected from the group consisting of Lys-Lys and Lys.

7. The peptide antagonist of claim 1, 2, 3 or 4 wherein B is Ser.

8. The peptide antagonist of claim 1, 2, 3 or 4 wherein C is Ser.

9. The peptide antagonist of claim 1, 2, 3 or 4 wherein A is Lys-Lys or Lys, B is Ser, and C is Ser.

10. The peptide antagonist of claim 1, 2, 3 of 4 wherein D is selected from the group consisting of Ser and Tyr.

11. The peptide antagonist of claim 9, wherein D is selected from the group consisting of Ser and Tyr.

12. The peptide antagonist of claim 1, 2, 3 or 4 wherein E is Val.

13. The peptide antagonist of claim 1, 2, 3 or 4 wherein F is selected from the group consisting of Asn-Asn and Asn.

14. The peptide antagonist of claim 5, wherein F is selected from the group consisting of Asn-Asn and Asn.

15. The peptide antagonist of claim 9, wherein F is selected from the group consisting of Asn-Asn and Asn.

16. The peptide antagonist of claim 12, wherein F is selected from the group consisting of Asn-Asn and Asn.

* * * * *